US009403884B2

(12) United States Patent
Brock et al.

(10) Patent No.: US 9,403,884 B2
(45) Date of Patent: Aug. 2, 2016

(54) PEPTIDES USEFUL AS CELL-PENETRATING PEPTIDES

(75) Inventors: Roland Brock, Kleve (DE); Rainer Fischer, Munich (DE); Mariola Fotin-Mleczek, Sindelfingen (DE); Hansjoerg Hufnagel, Soecking (DE); Norbert Windhab, Hofheim (DE)

(73) Assignee: Evonik Roehm GmbH, Hanau (DE)

( * ) Notice: Subject to any disclaimer, the term of this patent is extended or adjusted under 35 U.S.C. 154(b) by 503 days.

(21) Appl. No.: 13/557,706

(22) Filed: Jul. 25, 2012

(65) Prior Publication Data

US 2013/0108662 A1 May 2, 2013

Related U.S. Application Data

(62) Division of application No. 12/159,226, filed as application No. PCT/EP2006/010271 on Oct. 25, 2006, now abandoned.

(30) Foreign Application Priority Data

Dec. 30, 2005 (EP) .................................... 05028755

(51) Int. Cl.
*A61K 38/17* (2006.01)
*C07K 14/47* (2006.01)
*C07K 14/79* (2006.01)

(52) U.S. Cl.
CPC ................. *C07K 14/47* (2013.01); *C07K 14/79* (2013.01)

(58) Field of Classification Search
CPC ................................ C07K 14/47; A61K 38/17
USPC ......................................................... 514/21.4
See application file for complete search history.

(56) References Cited

U.S. PATENT DOCUMENTS

| 5,304,633 | A | 4/1994 | Tomita et al. |
| 5,741,957 | A | 4/1998 | Deboer et al. |
| 5,804,555 | A | 9/1998 | Tomita et al. |
| 6,066,725 | A | 5/2000 | DeBoer et al. |
| 6,399,570 | B1 | 6/2002 | Mann |
| 6,890,902 | B2 | 5/2005 | Svendsen et al. |

FOREIGN PATENT DOCUMENTS

| EP | 0 474 506 A1 | 3/1992 |
| EP | 0 643 074 A2 | 3/1995 |
| JP | 5-92994 | 4/1993 |
| JP | 6-256211 | 9/1994 |
| JP | 2002-519438 | 7/2002 |
| JP | 2002-520045 | 7/2002 |
| WO | WO 00/01730 | 1/2000 |
| WO | WO 00/04132 | 1/2000 |

OTHER PUBLICATIONS

Viejo-Diaz, Monica, Antimicrobial Agents and Chemotherapy (2005), 49(7), 2583-2588.*
Tomita, Mamoru, Acta Paediatrica Japonica (1994), 36(5), 585-91.*
U.S. Appl. No. 13/988,829, filed May 22, 2013, Hartwig, et al.
U.S. Appl. No. 13/648,846, filed Oct. 10, 2012, Seiler, et al.
Office Action issued May 7, 2014 in Canadian Patent Application No. 2,646,833.
International Search Report Issued Feb. 15, 2007 in PCT/EP2006/010271.
International Preliminary Report on Patentability and Written Opinion of the International Searching Authority Issued Jul. 1, 2008 in PCT/EP2006/010271.
Canadian Office Action Issued May 3, 2013 in Patent Application No. 2,646,833.
L. Moriarty, et al., "Factors contributing to the potency of antimicrobial cationic peptides from the N-terminal region of human lactoferrin", FEMS Microbiology Letters, vol. 239, No. 2, pp. 295-299, Oct. 15, 2004.
O. Aguilera, et al., "Permeabilizing action of an antimicrobial lactoferricin-derived peptide on bacterial and artificial membranes", FEBS Letters, vol. 462, No. 3, pp. 273-277, Dec. 3, 1999.
Vogel, et al., "Towards a structure-function analaysis of bovine lactoferricin and related tryptophan- and arginine-containing peptides", Biochemistry and Cell Biology, vol. 80, No. 1, pp. 49-63, Jan. 30, 2002.
Japanese Office Action issued May 18, 2011, in Patent Application No. 2008-547861 (English-language translation only).
David J. Schibli, et al., "Tryptophan-Rich Antimicrobial Peptides: Comparative Properties and Membrane Interactions", Biochem. Cell. Biol., vol. 80, XP009046767, 2002, pp. 667-677.
Jianglin He, et al., "Sequence Specificity and Transcriptional Activation in the Binding of Lactoferrin to DNA", Nature, vol. 373, Feb. 23, 1995, pp. 721-724.
Daniele Derossi, et al., "Trojan Peptides: The Penetratin System for Intracellular Delivery", Trends in Cell Biology, vol. 8, XP 002122131, Feb. 1998, pp. 84-87.
Chinese Office Action dated Feb. 24, 2011 as received in the corresponding Chinese Patent Application No. 200680049953.0 w/English Translation.
Shi Fang, et al., "Lactoferricin—active polypiptide with potential antibacterial activity" Chemistry of Life, vol. 24, No. 4, (2004), pp. 312-314 w/English Translation.
Japanese Office Action Issued Jun. 7, 2012 in Patent Application No. 2008-547861 (English translation only).

(Continued)

*Primary Examiner* — David Lukton
(74) *Attorney, Agent, or Firm* — Oblon, McClelland, Maier & Neustadt, L.L.P.

(57) ABSTRACT

A peptide having an amino acid sequence containing at least eight consecutive amino acids of the human lactoferrin protein or of the bovine lactoferrin protein. The peptide is suitable as a cell-penetrating peptide. A complex of the peptide and a cargo molecule non-covalently bound to the peptide. The cargo molecule may be a nucleic acid, an amino acid, a peptide, a protein, a carbohydrate, a lipid, or a small molecule. A method of penetrating or transfecting a cell using the complex.

10 Claims, 5 Drawing Sheets

(56) References Cited

OTHER PUBLICATIONS

Kenta Takeshima et al., "Translocation of Analogues of the Antimicrobial Peptides Magainin and Buforin across Human Cell Membranes", The Journal of Biological Chemistry, vol. 278, No. 2, 2003, pp. 1310-1315.

Natalia Nekhotiacva et al., "Cell entry and antimicrobial properties of eukaryotic cell-penetrating peptides", The FASEB Journal, vol. 18, No. 2, Dec. 4, 2003, 16 pages.

Office Action issued May 29, 2015 in Canadian Patent Application No. 2,646,833.

U.S. Appl. No. 14/357,322, filed May 9, 2014, Markowz, et al.

* cited by examiner

A

B

SEQUENCE LISTING

<160> NUMBER OF SEQ ID NOS: 33

<210> SEQ ID NO 1
<211> LENGTH: 711
<212> TYPE: PRT
<213> ORGANISM: Homo sapiens
<220> FEATURE:
<223> OTHER INFORMATION: human lactoferrin
<220> FEATURE:
<221> NAME/KEY: SIGNAL
<222> LOCATION: (1)..(19)

<400> SEQUENCE: 1

```
Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Lys
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Thr Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Ser Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320

Lys Asp Ser Ala Ile Gly Phe Ser Arg Val Pro Pro Arg Ile Asp Ser
                325                 330                 335

Gly Leu Tyr Leu Gly Ser Gly Tyr Phe Thr Ala Ile Gln Asn Leu Arg
```

```
              340              345              350
Ser Ser Glu Glu Glu Val Ala Ala Arg Arg Ala Arg Val Val Trp Cys
        355              360              365

Ala Val Gly Glu Gln Glu Leu Arg Lys Cys Asn Gln Trp Ser Gly Leu
    370              375              380

Ser Glu Gly Ser Val Thr Cys Ser Ser Ala Ser Thr Thr Glu Asp Cys
385              390              395              400

Ile Ala Leu Val Leu Lys Gly Glu Ala Asp Ala Met Ser Leu Asp Gly
                405              410              415

Gly Tyr Val Tyr Thr Ala Gly Lys Cys Gly Leu Val Pro Val Leu Ala
            420              425              430

Glu Asn Tyr Lys Ser Gln Gln Ser Ser Asp Pro Asp Pro Asn Cys Val
        435              440              445

Asp Arg Pro Val Glu Gly Tyr Leu Ala Val Ala Val Arg Arg Ser
    450              455              460

Asp Thr Ser Leu Thr Trp Asn Ser Val Lys Gly Lys Lys Ser Cys His
465              470              475              480

Thr Ala Val Asp Arg Thr Ala Gly Trp Asn Ile Pro Met Gly Leu Leu
                485              490              495

Phe Asn Gln Thr Gly Ser Cys Lys Phe Asp Glu Tyr Phe Ser Gln Ser
            500              505              510

Cys Ala Pro Gly Ser Asp Pro Arg Ser Asn Leu Cys Ala Leu Cys Ile
        515              520              525

Gly Asp Glu Gln Gly Glu Asn Lys Cys Val Pro Asn Ser Asn Glu Arg
    530              535              540

Tyr Tyr Gly Tyr Thr Gly Ala Phe Arg Cys Leu Ala Glu Asn Ala Gly
545              550              555              560

Asp Val Ala Phe Val Lys Asp Val Thr Val Leu Gln Asn Thr Asp Gly
                565              570              575

Asn Asn Asn Glu Ala Trp Ala Lys Asp Leu Lys Leu Ala Asp Phe Ala
            580              585              590

Leu Leu Cys Leu Asp Gly Lys Arg Lys Pro Val Thr Glu Ala Arg Ser
        595              600              605

Cys His Leu Ala Met Ala Pro Asn His Ala Val Val Ser Arg Met Asp
    610              615              620

Lys Val Glu Arg Leu Lys Gln Val Leu Leu His Gln Gln Ala Lys Phe
625              630              635              640

Gly Arg Asn Gly Ser Asp Cys Pro Asp Lys Phe Cys Leu Phe Gln Ser
                645              650              655

Glu Thr Lys Asn Leu Leu Phe Asn Asp Asn Thr Glu Cys Leu Ala Arg
            660              665              670

Leu His Gly Lys Thr Thr Tyr Glu Lys Tyr Leu Gly Pro Gln Tyr Val
        675              680              685

Ala Gly Ile Thr Asn Leu Lys Lys Cys Ser Thr Ser Pro Leu Leu Glu
    690              695              700

Ala Cys Glu Phe Leu Arg Lys
705              710

<210> SEQ ID NO 2
<211> LENGTH: 708
<212> TYPE: PRT
<213> ORGANISM: Bos sp.
<220> FEATURE:
<223> OTHER INFORMATION: bovine lactoferrin
<220> FEATURE:
```

<221> NAME/KEY: SIGNAL
<222> LOCATION: (1)..(19)

<400> SEQUENCE: 2

Met Lys Leu Phe Val Pro Ala Leu Leu Ser Leu Gly Ala Leu Gly Leu
1               5                   10                  15

Cys Leu Ala Ala Pro Arg Lys Asn Val Arg Trp Cys Thr Ile Ser Gln
                20                  25                  30

Pro Glu Trp Phe Lys Cys Arg Arg Trp Gln Trp Arg Met Lys Lys Leu
            35                  40                  45

Gly Ala Pro Ser Ile Thr Cys Val Arg Arg Ala Phe Ala Leu Glu Cys
        50                  55                  60

Ile Arg Ala Ile Ala Glu Lys Lys Ala Asp Ala Val Thr Leu Asp Gly
65                  70                  75                  80

Gly Met Val Phe Glu Ala Gly Arg Asp Pro Tyr Lys Leu Arg Pro Val
                85                  90                  95

Ala Ala Glu Ile Tyr Gly Thr Lys Glu Ser Pro Gln Thr His Tyr Tyr
            100                 105                 110

Ala Val Ala Val Val Lys Lys Gly Ser Asn Phe Gln Leu Asp Gln Leu
        115                 120                 125

Gln Gly Arg Lys Ser Cys His Thr Gly Leu Gly Arg Ser Ala Gly Trp
130                 135                 140

Ile Ile Pro Met Gly Ile Leu Arg Pro Tyr Leu Ser Trp Thr Glu Ser
145                 150                 155                 160

Leu Glu Pro Leu Gln Gly Ala Val Ala Lys Phe Phe Ser Ala Ser Cys
                165                 170                 175

Val Pro Cys Ile Asp Arg Gln Ala Tyr Pro Asn Leu Cys Gln Leu Cys
            180                 185                 190

Lys Gly Glu Gly Glu Asn Gln Cys Ala Cys Ser Ser Arg Glu Pro Tyr
        195                 200                 205

Phe Gly Tyr Ser Gly Ala Phe Lys Cys Leu Gln Asp Gly Ala Gly Asp
210                 215                 220

Val Ala Phe Val Lys Glu Thr Thr Val Phe Glu Asn Leu Pro Glu Lys
225                 230                 235                 240

Ala Asp Arg Asp Gln Tyr Glu Leu Leu Cys Leu Asn Asn Ser Arg Ala
                245                 250                 255

Pro Val Asp Ala Phe Lys Glu Cys His Leu Ala Gln Val Pro Ser His
            260                 265                 270

Ala Val Val Ala Arg Ser Val Asp Gly Lys Glu Asp Leu Ile Trp Lys
        275                 280                 285

Leu Leu Ser Lys Ala Gln Glu Lys Phe Gly Lys Asn Lys Ser Arg Ser
290                 295                 300

Phe Gln Leu Phe Gly Ser Pro Gly Gln Arg Asp Leu Leu Phe Lys
305                 310                 315                 320

Asp Ser Ala Leu Gly Phe Leu Arg Ile Pro Ser Lys Val Asp Ser Ala
                325                 330                 335

Leu Tyr Leu Gly Ser Arg Tyr Leu Thr Thr Leu Lys Asn Leu Arg Glu
            340                 345                 350

Thr Ala Glu Glu Val Lys Ala Arg Tyr Thr Arg Val Val Trp Cys Ala
        355                 360                 365

Val Gly Pro Glu Glu Gln Lys Lys Cys Gln Gln Trp Ser Gln Gln Ser
370                 375                 380

Gly Gln Asn Val Thr Cys Ala Thr Ala Ser Thr Thr Asp Asp Cys Ile
385                 390                 395                 400

```
Val Leu Val Leu Lys Gly Glu Ala Asp Ala Leu Asn Leu Asp Gly Gly
                405                 410                 415

Tyr Ile Tyr Thr Ala Gly Lys Cys Gly Leu Val Pro Val Leu Ala Glu
            420                 425                 430

Asn Arg Lys Ser Ser Lys His Ser Ser Leu Asp Cys Val Leu Arg Pro
                435                 440                 445

Thr Glu Gly Tyr Leu Ala Val Ala Val Val Lys Lys Ala Asn Glu Gly
            450                 455                 460

Leu Thr Trp Asn Ser Leu Lys Asp Lys Lys Ser Cys His Thr Ala Val
465                 470                 475                 480

Asp Arg Thr Ala Gly Trp Asn Ile Pro Met Gly Leu Ile Val Asn Gln
                485                 490                 495

Thr Gly Ser Cys Ala Phe Asp Glu Phe Phe Ser Gln Ser Cys Ala Pro
            500                 505                 510

Gly Ala Asp Pro Lys Ser Arg Leu Cys Ala Leu Cys Ala Gly Asp Asp
            515                 520                 525

Gln Gly Leu Asp Lys Cys Val Pro Asn Ser Lys Glu Lys Tyr Tyr Gly
            530                 535                 540

Tyr Thr Gly Ala Phe Arg Cys Leu Ala Glu Asp Val Gly Asp Val Ala
545                 550                 555                 560

Phe Val Lys Asn Asp Thr Val Trp Glu Asn Thr Asn Gly Glu Ser Thr
                565                 570                 575

Ala Asp Trp Ala Lys Asn Leu Asn Arg Glu Asp Phe Arg Leu Leu Cys
            580                 585                 590

Leu Asp Gly Thr Arg Lys Pro Val Thr Glu Ala Gln Ser Cys His Leu
            595                 600                 605

Ala Val Ala Pro Asn His Ala Val Val Ser Arg Ser Asp Arg Ala Ala
            610                 615                 620

His Val Lys Gln Val Leu Leu His Gln Gln Ala Leu Phe Gly Lys Asn
625                 630                 635                 640

Gly Lys Asn Cys Pro Asp Lys Phe Cys Leu Phe Lys Ser Glu Thr Lys
                645                 650                 655

Asn Leu Leu Phe Asn Asp Asn Thr Glu Cys Leu Ala Lys Leu Gly Gly
            660                 665                 670

Arg Pro Thr Tyr Glu Glu Tyr Leu Gly Thr Glu Tyr Val Thr Ala Ile
            675                 680                 685

Ala Asn Leu Lys Lys Cys Ser Thr Ser Pro Leu Leu Glu Ala Cys Ala
            690                 695                 700

Phe Leu Thr Arg
705

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Cys Phe Gln Trp Gln Arg Asn Met Arg Lys Val Arg Gly Pro Pro
1               5                   10                  15

Val Ser Cys Ile Lys Arg
            20
```

```
<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Phe Gln Trp Gln Arg Asn Met Arg Lys Val Arg Gly Pro Pro Val
1               5                   10                  15

Ser Cys

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Gln Trp Gln Arg Asn Met Arg Lys Val Arg Gly Pro Pro Val Ser
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe Gln Trp Gln Arg Asn Met Arg Lys Val Arg
1               5                   10

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Cys Phe Gln Trp Gln Arg Asn Val Arg Lys Val Arg Gly Pro Pro
1               5                   10                  15

Val Ser Cys Ile Lys Arg
            20

<210> SEQ ID NO 8
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Cys Phe Gln Trp Gln Arg Asn Ile Arg Lys Val Arg Gly Pro Pro
1               5                   10                  15

Val Ser Cys Ile Lys Arg
            20

<210> SEQ ID NO 9
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Norvaline

<400> SEQUENCE: 9

Lys Cys Phe Gln Trp Gln Arg Asn Xaa Arg Lys Val Arg Gly Pro Pro
1               5                   10                  15

Val Ser Cys Ile Lys Arg
            20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Cys Phe Gln Trp Gln Arg Asn Leu Arg Lys Val Arg Gly Pro Pro
1               5                   10                  15

Val Ser Cys Ile Lys Arg
            20

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Phe Gln Trp Gln Arg Asn Val Arg Lys Val Arg Gly Pro Pro Val
1               5                   10                  15

Ser Cys

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Phe Gln Trp Gln Arg Asn Ile Arg Lys Val Arg Gly Pro Pro Val
1               5                   10                  15

Ser Cys

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
```

<223> OTHER INFORMATION: Norvaline

<400> SEQUENCE: 13

Cys Phe Gln Trp Gln Arg Asn Xaa Arg Lys Val Arg Gly Pro Pro Val
1               5                   10                  15

Ser Cys

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Cys Phe Gln Trp Gln Arg Asn Leu Arg Lys Val Arg Gly Pro Pro Val
1               5                   10                  15

Ser Cys

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Norleucine

<400> SEQUENCE: 15

Cys Phe Gln Trp Gln Arg Asn Xaa Arg Lys Val Arg Gly Pro Pro Val
1               5                   10                  15

Ser Cys

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Gln Trp Gln Arg Asn Val Arg Lys Val Arg Gly Pro Pro Val Ser
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Phe Gln Trp Gln Arg Asn Ile Arg Lys Val Arg Gly Pro Pro Val Ser
1               5                   10                  15

<210> SEQ ID NO 18
<211> LENGTH: 16
<212> TYPE: PRT
<213> ORGANISM: Artificial Sequence
<220> FEATURE:

```
-continued

<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Norvaline

<400> SEQUENCE: 18

Phe Gln Trp Gln Arg Asn Xaa Arg Lys Val Arg Gly Pro Pro Val Ser
1               5                  10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Gln Trp Gln Arg Asn Leu Arg Lys Val Arg Gly Pro Pro Val Ser
1               5                  10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Norleucine

<400> SEQUENCE: 20

Phe Gln Trp Gln Arg Asn Xaa Arg Lys Val Arg Gly Pro Pro Val Ser
1               5                  10                  15

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Gln Trp Gln Arg Asn Val Arg Lys Val Arg
1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Gln Trp Gln Arg Asn Ile Arg Lys Val Arg
1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                          peptide
<220> FEATURE:
<221> NAME/KEY: MOD_RES
<222> LOCATION: (7)..(7)
<223> OTHER INFORMATION: Norvaline

<400> SEQUENCE: 23

Phe Gln Trp Gln Arg Asn Xaa Arg Lys Val Arg
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Phe Gln Trp Gln Arg Asn Leu Arg Lys Val Arg
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Norleucine

<400> SEQUENCE: 25

Phe Gln Trp Gln Arg Asn Xaa Arg Lys Val Arg
1               5                   10

<210> SEQ ID NO 26
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaatgcttcc aatggcaaag gaatatgaga aaagtgcgtg gccctcctgt cagctgcata      60
aagaga                                                                66

<210> SEQ ID NO 27
<211> LENGTH: 2136
<212> TYPE: DNA
<213> ORGANISM: Homo sapiens
<220> FEATURE:
<223> OTHER INFORMATION: human lactoferrin

<400> SEQUENCE: 27
atgaaacttg tcttcctcgt cctgctgttc ctcggggccc tcggactgtg tctggctggc      60
cgtaggagaa ggagtgttca gtggtgcgcc gtatcccaac ccgaggccac aaaatgcttc     120
caatggcaaa ggaatatgag aaaagtgcgt ggccctcctg tcagctgcat aaagagagac     180 tccccccatcc agtgtatcca ggccattgcg gaaaacaggg ccgatgctgt gacccttgat     240
ggtggtttca tatacgaggc aggcctggcc cctacaaac tgcgaccgt agcggcggaa       300 gtctacggga ccgaaagaca gccacgaact cactattatg ccgtggctgt ggtgaagaag     360
```

```
ggcggcagct ttcagctgaa cgaactgcaa ggtctgaagt cctgccacac aggccttcgc      420
aggaccgctg gatggaatgt ccctacaggg acacttcgtc cattcttgaa ttggacgggt      480
ccacctgagc ccattgaggc agctgtggcc aggttcttct cagccagctg tgttcccggt      540
gcagataaag gacagttccc caacctgtgt cgcctgtgtg cggggacagg ggaaaacaaa      600
tgtgccttct cctcccagga accgtacttc agctactctg gtgccttcaa gtgtctgaga      660
gacggggctg gagacgtggc ttttatcaga gagagcacag tgtttgagga cctgtcagac      720
gaggctgaaa gggacgagta tgagttactc tgcccagaca acactcggaa gccagtggac      780
aagttcaaag actgccatct ggcccgggtc ccttctcatg ccgttgtggc acgaagtgtg      840
aatggcaagg aggatgccat ctggaatctt ctccgccagg cacaggaaaa gtttggaaag      900
gacaagtcac cgaaattcca gctctttggc tcccctagtg ggcagaaaga tctgctgttc      960
aaggactctg ccattgggtt ttcgagggtg cccccgagga tagattctgg gctgtacctt     1020
ggctccggct acttcactgc catccagaac ttgaggaaaa gtgaggagga agtggctgcc     1080
cggcgtgcgc gggtcgtgtg tgtgcggtg ggcgagcagg agctgcgcaa gtgtaaccag     1140
tggagtggct tgagcgaagg cagcgtgacc tgctcctcgg cctccaccac agaggactgc     1200
atcgccctgg tgctgaaagg agaagctgat gccatgagtt tggatggagg atatgtgtac     1260
actgcatgca aatgtggttt ggtgcctgtc ctggcagaga actacaaatc ccaacaaagc     1320
agtgaccctg atcctaactg tgtggataga cctgtggaag gatatcttgc tgtggcggtg     1380
gttaggagat cagacactag ccttacctgg aactctgtga aaggcaagaa gtcctgccac     1440
accgccgtgg acaggactgc aggctggaat atccccatgg gcctgctctt caaccagacg     1500
ggctcctgca aatttgatga atatttcagt caaagctgtg cccctgggtc tgacccgaga     1560
tctaatctct gtgctctgtg tattggcgac gagcagggtg agaataagtg cgtgcccaac     1620
agcaacgaga gatactacgg ctacactggg gctttccggt gcctggctga gaatgctgga     1680
gacgttgcat tgtgaaaga tgtcactgtc ttgcagaaca ctgatggaaa taacaatgag     1740
gcatgggcta aggatttgaa gctggcagac tttgcgctgc tgtgcctcga tgcaaacgg     1800 aagcctgtga ctgaggctag aagctgccat cttgccatgg ccccgaatca tgccgtggtg     1860
tctcggatgg ataaggtgga acgcctgaaa caggtgctgc tccaccaaca ggctaaattt     1920
gggagaaatg gatctgactg cccggacaag ttttgcttat tccagtctga aaccaaaaac     1980
cttctgttca atgacaacac tgagtgtctg gccagactcc atggcaaaac aacatatgaa     2040
aaatatttgg gaccacagta tgtcgcaggc attactaatc tgaaaaagtg ctcaacctcc     2100
cccctcctgg aagcctgtga attcctcagg aagtaa                               2136
```

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)

<223> OTHER INFORMATION: Norleucine

<400> SEQUENCE: 28

Lys Cys Phe Gln Trp Gln Arg Asn Xaa Arg Lys Val Arg Gly Pro Pro
1               5                   10                  15

Val Ser Cys Ile Lys Arg
            20

<210> SEQ ID NO 29
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Cys Arg Arg Trp Gln Trp Arg Met Lys Lys Leu Gly Ala Pro Ser
1               5                   10                  15

Ile Thr Cys Val Arg Arg
            20

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Arg Arg Trp Gln Trp Arg Met Lys Lys Leu Gly Ala Pro Ser Ile
1               5                   10                  15

Thr Cys

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Gly Arg Lys Lys Arg Arg Gln Arg Arg Arg
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Gln Ile Lys Ile Trp Phe Gln Asn Arg Arg Met Lys Trp Lys Lys
1               5                   10                  15

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 33

Pro Glu Trp Phe Lys Cys Arg Arg Trp Gln Trp Arg Met Lys Lys Leu
1               5                   10                  15

Gly Ala
```

PEPTIDES USEFUL AS CELL-PENETRATING PEPTIDES

This application is a divisional of application Ser. No. 12/159,226, filed Dec. 1, 2008, now abandoned, which is a 371 of PCT/EP06/10271, filed Oct. 25, 2006, which claims foreign priority to EP 05028755.6, filed Dec. 30, 2005.

The present invention is related to a peptide which is suitable for use as a cell-penetrating peptide, complexes comprising the same and use thereof.

Cell-penetrating peptides (CPPs) such as the antennapedia-derived penetratin (Derossi et al., J. Biol. Chem., 269, 10444-10450, 1994) and the Tat peptide (Vives et al., J. Biol. Chem., 272, 16010-16017, 1997) are widely used tools for the delivery of cargo molecules such as peptides, proteins and oligonucleotides (Fischer et al., Bioconjug. Chem., 12, 825-841, 2001) into cells. Areas of application range from purely cell biological to biomedical research (Dietz and Bähr, Mol. Cell., Neurosci, 27, 85-131, 2004). Initially, cellular uptake was believed to occur by direct permeation of the plasma membrane (Prochiantz, Cuff. Opin. Cell Biol., 12, 400-406, 2000). In the past years, evidence has been accumulated that for several CPPs endocytosis contributes at least significantly to the cellular uptake for several CPPs (for a review, see Fotin-Mleczek et al., Curr. Pharm. Design, 11, 3613-3628, 2005). Given these recent results, the specification of a peptide as a CPP therefore does not imply a specific cellular import mechanism, but rather refers to a function as a peptide that, when conjugated to a cargo, either covalently or non-covalently, enhances the cellular uptake of the cargo molecule.

Although these CPPs have been proven to be in principle suitable for the delivery of peptides, proteins and oligonucleotides into cells, there is still a need to provide further CPPs allowing the delivery of such molecules as cargo molecules. In particular, there is a need for CPPs which (i) allow for a rapid release of cargo molecule from the endolysosomal pathway and (ii) avoid immunological reactions upon application in man.

The problem underlying the present invention is solved in a first aspect by a peptide having an amino acid sequence comprising at least 8 consecutive amino acids of the human lactoferrin protein or of the bovine lactoferrin protein, whereby the peptide is suitable to act as a cell-penetrating peptide.

In an embodiment of the first aspect the peptide comprises at least four cationic amino acids.

In an embodiment of the first aspect the human lactoferrin protein has an amino acid sequence according to SEQ.ID.No. 1 and the bovine lactoferrin protein has an amino acid sequence according to SEQ.ID.No. 2.

In an embodiment of the first aspect the peptide comprises at least two Cys residues or analogs thereof.

In a preferred embodiment of the first aspect the peptide comprises a disulfide bond created by two Cys residues or an analogous bond formed by the cysteine analogs.

In an embodiment of the first aspect the peptide comprises a moiety having an alpha-helical conformation of about 12 to 20 amino acids in length, and a moiety having a beta-sheet conformation of about 8 to 12 amino acids in length.

In an embodiment of the first aspect the peptide comprises from about 8 to about 60 amino acid residues.

In a preferred embodiment of the first aspect the peptide comprises from about 20 to about 45 amino acid residues.

In an embodiment of the first aspect the peptide has an amino acid sequence corresponding to amino acid positions 20 to 64 of the amino acid sequence according to SEQ.ID.No. 1.

In an embodiment of the first aspect the peptide has an amino acid sequence, whereby the N-terminal end of the peptide is an amino acid corresponding to amino acid positions 20 to 64 of the amino acid sequence according to SEQ.ID.No. 1 or SEQ. ID.No. 2.

In an embodiment of the first aspect the peptide is selected from the group comprising
   a peptide having the amino acid sequence KCFQWQRN-MRKVRGPPVSCIKR (SEQ.ID.No. 3),
   a peptide having the amino acid sequence CFQWQRNM-RKVRGPPVSC (SEQ.ID.No. 4),
   a peptide having the amino acid sequence FQWQRNM-RKVRGPPVS (SEQ.ID.No. 5),
   a peptide having the amino acid sequence FQWQRNM-RKVR (SEQ.ID.No. 6),
   a peptide having the amino acid sequence KCR-RWQWRMKKLGAPSITCVRR (SEQ ID No. 29), and
   a peptide having the amino acid sequence CRRWQWRMKKLGAPSITC (SEQ ID No. 30)
   and derivatives thereof.

In a preferred embodiment of the present invention the cell penetrating peptides comprise an amino acid sequence according to SEQ ID No. 3, SEQ ID No. 4, SEQ ID No. 29 or SEQ ID No. 30 or a sequence with an identity of at least 40%, preferred of at least 50%, in particular preferred of at least 75% or at least 90% to said sequences.

Peptides comprising SEQ ID No. 3, SEQ ID No. 4, SEQ ID No. 29 or SEQ ID No. 30 with at least 40% identity are preferred characterized by the replacement or deletion of 1 to 13 amino acids of SEQ ID No. 3 or SEQ ID No. 29 respectively 1 to 10 amino acids of SEQ ID No. 4 or SEQ ID No. 30. Wherein sequences with a replacement of one or more amino acids with homologue amino acids are of increased interest.

The peptides comprising an amino acid sequence according to SEQ ID No. 3, SEQ ID No. 4, SEQ ID No. 29 or SEQ ID No. 30 or a sequence with at least 40% identity comprise at least 8 amino acids (peptides derived from SEQ ID No. 4 or SEQ ID No. 30) respectively 9 amino acids (peptides derived SEQ ID No. 3 or SEQ ID No. 29). Said peptides have preferred between 10 and 45 amino acids and preferred between 14 and 25 amino acids.

Preferred peptides comprising an amino acid sequence according to SEQ ID No. 3, SEQ ID No. 4, SEQ ID No. 29 or SEQ ID No. 30 possess a cationic charge, in particular of at least four cationic amino acids located in SEQ ID No. 3, SEQ ID No. 4, SEQ ID No. 29 or SEQ ID No. 30. A further preferred feature of said peptides is the presence of at least two cysteines or cysteine analogous which may form a disulfide bridge or an analogue bridge. Both cysteines or its analogous enclose at least 6 amino acids, preferably between 12 and 43 amino acids.

In a preferred embodiment of the first aspect the peptide is a derivative of the peptides according to any of SEQ.ID.No. 2 to 5, whereby the methionine residues is replaced by an amino acid selected from the group comprising valine, isoleucine, norvaline, leucine and norleucine.

In a more preferred embodiment of the first aspect the peptide is a peptide having an amino acid sequence selected from the group comprising KCFQWQRNVRKVRGPPVSCIKR (SEQ.ID.No. 7)

-continued

KCFQWQRNIRKVRGPPVSCIKR (SEQ.ID.No. 8)

KCFQWQRNXRKVRGPPVSCIKR, (SEQ.ID.No. 9)
whereby X is norvaline,

KCFQWQRNLRKVRGPPVSCIKR, (SEQ.ID.No. 10)

KCFQWQRNXRKVRGPPVSCIKR, (SEQ.ID.No. 28)
whereby X is norleucine,

CFQWQRNVRKVRGPPVSC, (SEQ.ID.No. 11)

CFQWQRNIRKVRGPPVSC, (SEQ.ID.No. 12)

CFQWQRNXRKVRGPPVSC, (SEQ.ID.No. 13)
whereby X is norvaline,

CFQWQRNLRKVRGPPVSC, (SEQ.ID.No. 14)

CFQWQRNXRKVRGPPVSC, (SEQ.ID.No. 15)
whereby X is norleucine,

FQWQRNVRKVRGPPVS, (SEQ.ID.No. 16)

FQWQRNIRKVRGPPVS, (SEQ.ID.No. 17)

FQWQRNVRKVRGPPVS, (SEQ.ID.No. 18)
whereby X is norvaline,

FQWQRNLRKVRGPPVS, (SEQ.ID.No. 19)

FQWQRNXRKVRGPPVS, (SEQ.ID.No. 20)
whereby X is norleucine,

FQWQRNVRKVR, (SEQ.ID.No. 21)

FQWQRNIRKVR, (SEQ.ID.No. 22)

FQWQRNXRKVR, (SEQ.ID.No. 23)
whereby X is norvaline,

FQWQRNLRKVR, (SEQ.ID.No. 24)
and

FQWQRNXRKVR, (SEQ.ID.No. 25)
whereby X is norleucine.

In an embodiment of the first aspect the derivatives have a linkage group preferably selected from the group comprising thioethers, whereby the linkage group replaces the disulfide bond formed by these Cys residues.

In an embodiment of the first aspect, the peptide is radioactively labelled, preferably by having incorporated a radioactively labelled amino acid, whereby more preferably the radioactively labelled amino acid is a tritium-labelled amino acid.

In an embodiment of the first aspect the peptide further comprises a moiety which is suitable for detection using a method for detection, whereby such moiety is preferably selected from the group comprising fluorophores, radioactive tracers and haptens, whereby preferably the hapten is biotin.

The problem underlying the present invention is also solved in a second aspect by a complex comprising a peptide selected from the group comprising a peptide according to the first aspect, human lactoferrin and bovine lactoferrin, and a cargo molecule.

In an embodiment of the second aspect the cargo molecule is covalently or non-covalently bound to the peptide.

In an embodiment of the second aspect the cargo molecule is selected from the group comprising nucleic acids, amino acids, peptides, proteins, carbohydrates, lipids, and small molecules and mixtures of any of thereof.

In an embodiment of the second aspect the cargo molecule is present as or part or a structure, whereby the structure is selected from the group comprising nanoparticles, microparticles, liposomes and micelles.

In a preferred embodiment of the second aspect the nucleic acid is a nucleic acid selected from the group comprising DNA molecules, RNA molecules, PNA molecules, siRNA molecules, antisense molecules, ribozymes, aptamers, spiegelmers and decoy molecules.

In an alternative preferred embodiment of the second aspect the peptide is selected from the group comprising peptides for vaccination.

In a further alternative preferred embodiment of the second aspect the nucleic acid is a nucleic acid-based vaccine.

In a still further alternative preferred embodiment of the second aspect the nano-particles and/or the micro-particles comprise or consist of a pharmaceutically active compound.

The problem underlying the present invention is also solved in a third aspect by a composition comprising at least a peptide selected from the group comprising a peptide according to the first aspect, human lactoferrin and bovine lactoferrin, and a cargo molecule.

The problem underlying the present invention is also solved in a fourth aspect by a composition comprising a complex according to the second aspect.

The problem underlying the present invention is also solved in a fifth aspect by a nucleic acid coding for a peptide according to the first aspect, preferably having a nucleic acid sequence according to SEQ.ID.No. 26 or SEQ.ID.No. 27.

The problem underlying the present invention is also solved in a sixth aspect by a composition comprising a nucleic acid according to the fifth aspect and a cargo molecule.

In a preferred embodiment of the sixth aspect the cargo molecule is a nucleic acid and more particularly a RNA suitable for vaccination.

In a preferred embodiment of the sixth aspect the cargo molecule is a nucleic acid coding for a peptide.

In a preferred embodiment of the sixth aspect the nucleic acid according to the fifth aspect is operably linked to the nucleic acid coding for a peptide.

In a more preferred embodiment of the sixth aspect the nucleic acid according to the fifth aspect and the nucleic acid coding for a peptide are linked in-frame.

In an embodiment of the sixth aspect the peptide is a pharmaceutically active agent.

The problem underlying the present invention is also solved in a seventh aspect by the use of a peptide according to the first aspect as a cell-penetrating peptide.

The problem underlying the present invention is also solved in an eighth aspect by the use of human lactoferrin or a functional derivative thereof or of bovine lactoferrin or a functional derivative thereof as a cell-penetrating peptide.

In an embodiment of the eight aspect the human lactoferrin has an amino acid sequence comprising amino acid positions 20 to 711 of the amino acid sequence according to SEQ. ID. No. 1 or functional derivative thereof and/or the bovine lactoferrin has an amino acid sequence comprising amino acid positions 20 to 708 of the amino acid sequence according to SEQ.ID.No. 2 or a functional derivative thereof.

The problem underlying the present invention is also solved in a ninth aspect by the use of a peptide according to the first aspect as a transfection agent.

The problem underlying the present invention is also solved in an tenth aspect by the use of human lactoferrin or a functional derivative thereof or of bovine lactoferrin or a functional derivative thereof as a transfection agent.

In an embodiment of the tenth aspect the human lactoferrin has an amino acid sequence comprising amino acid positions 20 to 711 of the amino acid sequence according to SEQ. ID. No. 1 and/or the bovine lactoferrin has an amino acid sequence comprising amino acid positions 20 to 708 of the amino acid sequence according to SEQ.ID.No. 2 or a functional derivative thereof.

The problem underlying the present invention is also solved in an eleventh aspect by the use of a composition according to the third, the fourth, and the sixth aspect for the manufacture of a medicament.

In an embodiment of the eleventh aspect the cargo molecule is a pharmaceutically active agent.

The problem underlying the present invention is also solved in a twelfth aspect by the use of a composition according to the third, the fourth, and the sixth aspect for the manufacture of a diagnostic agent.

In an embodiment of the twelfth aspect the cargo molecule is a diagnostic marker.

The present inventors have surprisingly found that human and bovine lactoferrin and more specifically peptides thereof, which are also referred to herein as the peptides according to the present invention, are suitable to act as cell-penetrating peptides (CPP) and may thus deliver cargo molecules to the cytoplasm of a cell. A CPP is preferably any peptide or protein which is suitable to penetrate a cellular membrane, more preferably the plasma membrane of a mammalian cell. However, it is to be understood that preferably the term CPP does not imply a specific cellular import mechanism. More specifically, the present inventors have realized that specific peptides derived from human lactoferrin are released from the endolysosomal compartments in a highly efficient manner which in turn goes along with a highly efficient release of any cargo molecule(s). Once the cargo molecules are available in the cytoplasma they may exert any effect associated therewith. Insofar, the polypeptides according to the invention provide for an efficient means for influencing the biological mechanisms and pathways of a cell which can be used for both research as well as therapeutic and diagnostic applications. As used herein and if not indicated to the contrary, the term peptides according to the present invention preferably also comprises human and bovine lactoferrin as preferably defined herein.

The peptides according to the present invention are, in principle, fragments of the human or bovine lactoferrin, or a derivative thereof. Because of this origin, the peptides according to the present invention exhibit, apart from them being suitable to deliver cargo molecules to the cytoplasm, a beneficial immunological profile insofar as the respective peptides will not elicit an immune response in a human or bovine host exposed to the respective peptides according to the present invention.

Human lactoferrin (hLF) is a 77 kDa iron-binding glycoprotein of 692 amino acids that constitutes 15% of the amount of protein contained in human mother milk and can also be found in low concentrations in blood plasma (Hemet and Simonovits, Haematologia (Budap.) 18, 3-121985). The bovine homologue (bLF) consists of 688 amino acids and shares 68% amino acid identity with hLF (Crichton, Adv. Protein Chem. 40, 281-363, 1990). However, only 0.5-1% of bovine milk protein is bLF. For both proteins antimicrobial (Orsi, Biometals 17, 189-196, 2004; Ward and Conneely, Biometals 17, 203-208, 2004), antifungal, LPS binding (Vogel et al., Biochem. Cell Biol. 80, 49-63, 2002) and antiviral properties (Berkhout et al., Biometals 17, 291-294, 2004) have been reported as well as several enzymatic activities like DNase, RNase, ATPase and phosphatase activity (Kanyshkova et al., Eur. J. Biochem. 270, 3353-3361, 2003). Lactoferrin (LF) proteins also act as transcription factors (He and Furmanski, Nature 373, 721-724, 1995) and have an impact on immune regulation by inducing the secretion of interleukins (Sorimachi et al., Biochem. Mol. Biol. Int. 43, 79-87, 1997; Vogel et al., 2002).

The peptides according to the present invention are preferably fragments of the N-terminal region of the human or bovine lactoferrin. Further structural features which either individually or in any combination may be realized by the peptides according to the present invention are disclosed in the following.

Preferably, such fragment and thus a peptide according to the present invention contains at least four cationic amino acid residues. More preferably, these fragments are cationic, i.e. have an overall positive charge at physiological pH values.

The peptides according to the present invention may share a combination of secondary structures such as an alpha helix and a beta sheet. In particular such helix and such sheet form individual moieties of the peptides. Most preferably, the peptides comprise a helix-turn-sheet structure. The length of such moieties typically range from 12-20 amino acids and 8 to 12 amino acids in length for the moieties with alpha-helix and beta-sheet conformation, respectively.

A further feature inherent to preferred embodiments of the peptides according to the present invention is the presence of at least two Cys residues. Such Cys residues are spaced apart from each other by a number of intermittent amino acids. Preferably the number of such intermittent amino acids ranges from 8 to 20 amino acids, more preferably 14 to 18 and is most preferably 16. In a still further embodiment the two Cys residues are located at the N-terminal end and at the C-terminal end of the peptide according to the present invention. It is within the present invention that the respective Cys residues, either individually or in combination, are located at or close to the ends of the peptide, i.e. form the N-terminal end and the C-terminal of the peptide. Alternatively, one or both of said Cys ends do not form the respective end of the peptide, but the peptide comprises further amino acids upstream of the respective Cys residue in case of the N-terminal end, or downstream of the respective Cys residue in case of the C-terminal end. In a still more preferred embodiment the two Cys residue form an intramolecular disulphide bond, whereby such disulphide bond preferably exists under conditions existing when applying or using the peptides according to the present invention as CPPs. It is known to the ones skilled in the art how to generate such disulphide bond upon or during synthesis of the respective peptide. In an alternative embodiment, the two Cys residues form an intermolecular disulphide bond.

In a still further embodiment the disulphide bond, if any, is replaced by a moiety which structurally and functionally replaces the disulfide bond, however, is not subject to reductive cleavage. Such moiety is exemplified by, but not limited to, a methylene group (JACS, 1985, 107, 2986-2987, Bioorg. Med. Chem. Letter 1999, 9, 1767-1772, J. Med. Chem., 2002, 45, 1767-1777), a thioether bridge (Yu et al. Tetrahedron Lett. 1998, 39, 6633-6636), a carbonyl bridge (Pawlak et al. J. Pept. Sci. 2001, 7, 128-140), and a longer aliphatic chain (Tetrahedron Lett. 2001, 42, 5804-5804), whereby each of said moiety replaces the disulfide bond. Depending on the specific protocol and moiety used for connecting the two amino acid residues, the replacement of cysteine residues by other building blocks, e.g. homoserine, may be required (Yu et al. Tetrahedron Lett. 1998, 39, 6633-6636) as will be acknowledged by the ones skilled in the art. Preferably the length of the longer aliphatic chain is from about 2 to about 10 C atoms, whereby this range comprises any integer length in-between.

The length of the peptides according to the present invention preferably ranges from about 8 amino acid residues to about 60 amino acid residues. More preferably the length ranges from 15 to 45 amino acid residues, more preferable from 18 to 22 amino acid residues. It will, however, be acknowledged by the ones skilled in the art that the length of the peptides is not necessarily limited thereto and derivatives thereof can be created by the ones skilled in the art using the technical guidance provided herein. Any modification insofar is within the scope of the present invention which still provides for peptides which act or can act as CPPs.

In a further preferred embodiment the peptides according to the present invention are fragments of the human or bovine lactoferrin. Preferably the human lactoferrin has the amino acid according to SEQ.ID.No. 1, and the bovine lactoferrin the amino acid sequence according to SEQ.ID.No. 2. More preferably, the peptides according to the present invention correspond in their amino acid sequence to a sequence of amino acids comprised or defined by amino acid positions 20 to 64 of the sequence according to SEQ.ID.No. 1 or of the sequence according to SEQ.ID.No. 2. However, it is also within the present invention that only part of the peptides according to the present invention is located within the above defined range of the amino acid sequence of human or bovine lactoferrin.

In a more preferred embodiment, the peptides according to the present invention are derived from the human or bovine lactoferrin as specified in the previous paragraphs and share one or several, preferable all of the further structural features disclosed herein.

In a further embodiments the peptides according to the present invention are derivatives of any of the peptides according to the present invention described herein and in particular as disclosed in the previous paragraphs. It will be acknowledged by the ones skilled in the art that the amino acid sequence of said peptides may be changed without that said peptides lose the characteristic of being functional as a CPP. Preferable such changes are made to the amino acid sequence. More preferably such change comprise the replacement of an amino acid of a distinct category by another amino acid of the same category. Such categories are preferably neutral amino acids, hydrophobic amino acids (in particular including aliphatic amino acids), cationic amino acids, anionic amino acids, thiol-containing amino acids, aromatic amino acids and heterocyclic amino acids. Hydrophobic amino acids (including aliphatic amino acids) are preferred selected from the group consisting of glycine, alanine, valine, leucine and isoleucine, aromatic amino acids are preferred selected from the group consisting of phenylalanine, tyrosine and tryptophane, ionic amino acids are preferred selected from the group of cationic amino acids like lysine, arginine, histidine and anionic amino acids like aspartat and glutamat, neutral amino acids are preferred selected from the group serine, threonine, asparagines, glutamine and methionine, thiol-containing amino acids are preferred cysteine and methionine and heterocyclic amino acids are preferred proline and histidine. Especially the methionine residue in position 46 may be exchanged for an aliphatic residue such as, for example, but not limited to, valine, norvaline, leucine or norvaline. As peptides may be obtained by protocols of organic synthesis, amino acid replacements are not limited to those of proteinogenic amino acids. Any building block including, but not limited to, non-proteinogenic amino acids and beta-amino acids, that may be incorporated by suitable chemical procedures may be included in the peptide.

Particularly preferred peptides according to the present invention are those having an amino acid sequence according to SEQ.ID.No. 3 and according to SEQ.ID.No. 4, and respective derivatives thereof.

It is within the present invention that if a peptide according to the present invention is the human or bovine lactoferrin, such peptide, in a preferred embodiment, also comprises fragments of the full-length human or bovine lactoferrin protein. Such fragments are preferably functionally active fragments. As used herein a functionally active fragment of the human or bovine lactoferrin is or comprises a part of the amino acid sequence according to SEQ.ID.No. 1 or SEQ.ID.No. 2 under the provision that such fragment still exhibits a CPP activity, preferably a CPP activity as defined herein. Preferably the activity of said peptide as a CPP, or CPP activity, may be determined by conjugation of the respective peptide to a fluorochrome or hapten that in this case serves both as a reporter group and as a cargo molecule and enables the detection and quantification of cellular uptake by methods known to those familiar with the art. Such methods include but are not limited to (i) flow cytometry and fluorescent microscopy for fluorophores serving as reporter group or (ii) fixation and permeabilization of cells followed by incubation with a reagent suitable for the detection for haptens serving as a reporter group. Alternatively, the CPP may be radioactively labeled, e.g. by incorporation of radioactively labeled amino acids and the cellular uptake determined by radiography. The latter method enables the determination of uptake and distribution for the peptides alone, without any cargo. It is understood that to the degree the respective method allows so, the uptake and distribution may also be determined and quantitated for tissues and whole organisms. Alternatively, the uptake may be determined indirectly by means of the biological activity of a cargo molecule conjugated to the CPP and with the cargo molecule exerting its biological activity only if the molecule enters the cell and reaches a particular subcellular localization such as the cytoplasm or nucleus.

In a further embodiments the peptides according to the present invention further comprise a moiety which is suitable for detection. More specifically, such moiety allows for the detection of the peptide. The moiety may be any group suitable for such purpose. Respective moieties are known to the ones skilled in the art and comprise, however, are not limited to, fluorophores, such as for example carboxyfluorescein, or biotin. Preferably the detection occurs by means of fluorescence. Alternatively, the detection may also occur by means of radioactivity, e.g. after incorporation of $^{125}$Iodine by protocols known to those skilled in the art. Detection may occur at the level of an individual cell, a tissue, an organ or an animal. Preferably the animal is a mammal and more preferably selected from the group comprising a dog, a cat, a sheep, a goat, a rat, a mouse, a cow, a horse and a human being.

In a further aspect of the present invention the peptides according to the present invention form a complex together with a cargo molecule. Such cargo molecule may be any cargo molecule as defined herein. The complex can be either a covalent or a non-covalent complex comprising at least one peptide according to the present invention and at least one cargo molecule. It is also within in the present invention that the complex comprises more than one peptide according to the present invention, i.e. a plurality of such peptides, whereby the plurality of the peptides may comprise a plurality of the same or of different peptides. Also, the complex according to the present invention may also comprise more than one cargo molecule, whereby the plurality of the cargo molecules may comprise a plurality of the same or of different cargo molecules.

In one embodiment, the complex between the peptide(s) according to the present invention and the cargo molecule(s) is formed by covalent bonds. Such covalent bonds are preferably formed between either suitable reactive group of the peptide and the cargo and more preferable between a terminus of the peptide according to the present invention and the cargo molecule(s). Depending on the chemical nature or the cargo molecules, the moiety, group or radical with which such covalent bond is formed varies and it is within the skills of a person of the art to create such bond. In one embodiment, the covalent bond may be an amide bond formed between the carboxy group of the C-terminal amino acid of a peptide according to the present invention and the alpha amino group of the N-terminal amino acid of a peptide constituting a cargo molecule. Alternatively, the complex can be formed based on non-covalent bond(s). Such non-covalent bonds can be ionic bonds, hydrogen bonds or hydrophobic interaction or a combination of such bonds. In one embodiment such non-covalent bonds may be formed by a stretch of lysine residues, attached by covalent bonds to a peptide according to the present invention and the phosphate backbone of a oligonucleotide. Preferably the stretch of lysine consists of about 5 to 15 lysine residues.

The cargo molecules are, in principle, not limited with regard to size, chemical nature and/or function. In accordance therewith the cargo molecule may be selected from the group comprising nucleic acids, peptides, molecules, lipids, carbohydrates, nano- and micro-particles and combinations thereof. In a preferred embodiment, the cargo molecules are within the bounds set by applications in cell biology or therapeutical applications.

In an embodiment the nucleic acid is any polymer consisting of at least two nucleotides which are covalently linked. In an embodiment a nucleic acid can be a DNA molecule or a RNA molecule or a mixture thereof. It is also within the present invention that the nucleic acid consists of L-nucleotides, D-nucleotides or mixtures In a further embodiment, the base moiety, the sugar moiety and/or the phosphate moiety of the individual nucleotide can be individually and independently modified for each and any of the nucleotides forming the nucleic acid or the respective analog. Particularly preferred modified sugar moieties are those having a methyl, methoxy, ethyl or ethoxy group at the 2' atom of the sugar moiety. Particularly preferred modified phosphat moieties are phosphothioates. In another preferred embodiment, peptide nucleic acids are employed In another preferred embodiment the cargo molecule is an amino acid, originating from the group of L- or D-amino acids. The amino acid may be any amino acid, whether naturally occurring or non-natural.

In another preferred embodiment the cargo molecule is a peptide, consisting of at least two amino acids which are covalently linked, preferably through a peptide bond. In an embodiment the peptide consists of L-amino acids, D-amino acids or mixtures thereof. The amino acids may be any amino acids, whether naturally occurring or non-natural. In a preferred embodiment the term peptide thus also comprises peptides and proteins as generally understood in the art. The peptides or proteins may be purified from natural sources, obtained through organic synthesis or obtained by conjugation of synthetic amino acids or peptides to peptides or proteins obtained from natural sources by protocols familiar to those skilled in the art and exemplified but not limited to native chemical ligation. Preferably, peptides will have a length of 2 to 40 amino acids, more preferably of 2 to 20 amino acids and most preferably of 4 to 15 amino acids. As used herein, the term protein preferably refers to a polypeptide containing secondary structure and more preferably tertiary structure.

In another preferred embodiment the cargo molecule is a small molecule, whereby a small molecule is preferably a molecule having a molecular weight of 1000 D or less and more preferably representing a drug or a drug candidate. A particularly preferred class of small molecules are heterocyclic small molecules.

In another preferred embodiment the cargo molecule is a lipid or a substructure of a lipid such as a moiety thereof. Preferably, a molecule of this class will exert a particular function once acting on the cell either inside or in the plasma membrane. An example for the former is diacylglycerol. This example illustrates that a lipid exerting such particular function is preferably selected from the group comprising intracellular messengers. An example for the latter and thus representing a possible cargo molecule is a lipopeptide, preferably a lipopeptide with a S-[2,3-bis(palmitoyloxy)-(2RS)-propyl]-N-palmitoyl-(R)-cysteinyl-(S)-seryl-tetra-(S)-lysine moiety and most preferably a peptide with a S-[2,3-bis(palmitoyloxy)-(2RS)-propyl]-N-palmitoyl-(R)-cysteinyl-(S)-seryl-tetra-(S)-lysine acting as an agonist or antagonist of a Toll-like receptor.

In another preferred embodiment the cargo molecule is a carbohydrate.

In another preferred embodiment the cargo is a contrasting agent used for magnetic resonance imaging. Such contrasting agents are for example but not limited to gadolinium (III)-DTPA (diethylenetriamine-pentaacetic acid) or gadolinium (III)-DOTA (1,4,7,10-Tetraazacyclododecane-1,4,7,10-tetraacetic acid)

In another preferred embodiment, the cargo molecule is a particle. A particle may be a polymer particle, consisting, for example, of cross-linked polystyrene, cross-linked N-(2-hydroxypropyl)methacrylamide, cross-linked dextran, a liposome, or a micelle. Preferably, the particle serves as a carrier or container for a functional molecule. The functional molecule may be any molecules exerting a function inside cells, e.g. chemotherapeutics and oligonucleotides and preferably those that may also serve as cargo molecules for the peptides according to the present invention. In general coupling of the functional molecule to the particle, respectively loading of the functional molecules into the particle, is intended to improve the pharmacokinetic properties of the functional molecule, e.g. by prolonging its circulation in the organism while coupling of the peptide(s) according to the present invention mediates the delivery of these functional molecules into cells. In addition to the peptide(s) according to the present invention, the particles may further be modified by a moiety or a molecule that mediate a targeting of the particles to specific cells. One example for such targeting are antibodies directed against proteins enriched on the surface of cancer cells. In one embodiment the particle may have a ferromagnetic core. Such particles may be used in applications such as magnetic fluid hyperthermia (Jordan et al., Int J Hyperthermia, 12, 705-722, 1996)

In another preferred embodiment the cargo molecule is a quantum dot. Coupling of the peptide(s) according to the present invention to the quantum dot may be achieved by covalent coupling, for example by amide bond formation between suitable functionalities on the peptide and the quantum dot or by non covalent interactions, for example between a biotin moiety and a streptavidin molecule coupled to the quantum dot. In one example a cell-penetrating peptide was covalently linked to a quantum dot by elongation of the cell-penetrating peptide with a cysteine residue and coupling to amino-functionalized quantum dots using a heterobifunktional linker (S. Santra et al., ChemComm, 2005, 3144-3146).

In a further embodiment, the cargo molecules can be defined in functional terms.

In a particular embodiment the cargo molecule is a siRNA molecule.

siRNA molecules are small interfering RNAs directed to a target nucleic acid, preferably mRNA, coding for the target molecule. siRNA is a double stranded RNA having typically a length of about 21 to about 23 nucleotides. The sequence of one of the two RNA strands corresponds to the sequence of the target nucleic acid to be degraded. In other words, knowing the nucleic acid sequence of the target molecule, preferably the mRNA sequence, a double stranded RNA may be designed with one of the two strands being complementary to said mRNA of the target molecule and, upon application of said siRNA to a system containing the gene, genomic DNA, hnRNA or mRNA coding for the target molecule, the respective corresponding target nucleic acid will be degraded and thus the level of the respective protein be reduced. The basic principles of designing, constructing and using said siRNA as medicament and diagnostic agent, respectively, is, among others, described in international patent applications WO 00/44895 and WO 01/75164.

In a particular embodiment the cargo molecule is a ribozyme.

Ribozymes are catalytically active nucleic acids which preferably consist of RNA which basically comprises two moieties. The first moiety shows a catalytic activity whereas the second moiety is responsible for the specific interaction with the target nucleic acid. Upon interaction between the target nucleic acid and the second moiety of the ribozyme, typically by hybridisation and Watson-Crick base pairing of essentially complementary stretches of bases on the two hybridising strands, the catalytically active moiety may become active which means that it catalyses, either intramolecularly or intermolecularly, the target nucleic acid in case the catalytic activity of the ribozyme is a phosphodiesterase activity. Subsequently, there may be a further degradation of the target nucleic acid which in the end results in the degradation of the target nucleic acid as well as the protein derived from the said target nucleic acid due to a lack of newly synthesized protein corresponding to the target nucleic acid and a turn-over of prior existing respective protein. Ribozymes, their use and design principles are known to the one skilled in the art, and, for example described in Doherty and Doudna (Ribozym structures and mechanism. Annu ref. Biophys. Biomolstruct. 2001; 30:457-75) and Lewin and Hauswirth (Ribozyme Gene Therapy: Applications for molecular medicine. 2001 7: 221-8).

In a particular embodiment the cargo molecule is an antisense molecule.

The use of antisense oligonucleotides for the manufacture of a medicament and as a diagnostic agent, respectively, is based on a similar mode of action as the one of siRNA molecules and ribozymes. Basically, antisense oligonucleotides hybridise based on base complementarity, with a target RNA, preferably with a mRNA, thereby activate RNase H. RNase H is activated by both phosphodiester and phosphorothioate-coupled DNA. Phosphodiester-coupled DNA, however, is rapidly degraded by cellular nucleases with the exception of phosphorothioate-coupled DNA. These resistant, non-naturally occurring DNA derivatives do not inhibit RNase H upon hybridisation with RNA. In other words, antisense polynucleotides are only effective as DNA RNA hybrid complexes. Examples for this kind of antisense oligonucleotides are described, among others, in U.S. Pat. No. 5,849,902 and U.S. Pat. No. 5,989,912. In other words, based on the nucleic acid sequence of the respective target molecule, either from the target protein from which a respective nucleic acid sequence may in principle be deduced, or by knowing the nucleic acid sequence as such, particularly the mRNA, suitable antisense oligonucleotides may be designed base on the principle of base complementarity.

Particularly preferred are antisense-oligonucleotides which have a short stretch of phosphorothioate DNA (3 to 9 bases). A minimum of 3 DNA bases is required for activation of bacterial RNase H and a minimum of 5 bases is required for mammalian RNase H activation. In these chimeric oligonucleotides there is a central region that forms a substrate for RNase H that is flanked by hybridising "arms" comprised of modified nucleotides that do not form substrates for RNase H. The hybridising arms of the chimeric oligonucleotides may be modified such as by 2"-O-methyl or 2'-fluoro. Alternative approaches used methylphosphonate or phosphoramidate linkages in said arms. Further embodiments of the antisense oligonucleotide useful in the practice of the present invention are P-methoxyoligonucleotides, partial P-methoxyoligodeoxyribonucleotides or P-methoxyoligonucleotides.

In a particular embodiment the cargo molecule is an aptamer or a spiegelmer.

Aptamers are D-nucleic acids which are either single stranded or double stranded and which specifically interact with a target molecule. The manufacture or selection of aptamers is, e.g., described in European patent EP 0 533 838. Basically the following steps are realized. First, a mixture of nucleic acids, i.e. potential aptamers, is provided whereby each nucleic acid typically comprises a segment of several, preferably at least eight subsequent randomised nucleotides. This mixture is subsequently contacted with the target molecule whereby the nucleic acid(s) bind to the target molecule, such as based on an increased affinity towards the target or with a bigger force thereto, compared to the candidate mixture. The binding nucleic acid(s) are/is subsequently separated from the remainder of the mixture. Optionally, the thus obtained nucleic acid(s) is amplified using, e.g. polymerase chain reaction. These steps may be repeated several times giving at the end a mixture having an increased ratio of nucleic acids specifically binding to the target from which the final binding nucleic acid is then optionally selected. These specifically binding nucleic acid(s) are referred to aptamers. It is obvious that at any stage of the method for the generation or identification of the aptamers samples of the mixture of individual nucleic acids may be taken to determine the sequence thereof using standard techniques. It is within the present invention that the aptamers may be stabilized such as, e.g., by introducing defined chemical groups which are known to the one skilled in the art of generating aptamers. Such modification may for example reside in the introduction of an amino group at the 2'-position of the sugar moiety of the nucleotides. Aptamers are currently used as therapeutical agens. However, it is also within the present invention that the thus selected or generated aptamers may be used for target validation.

The generation or manufacture of spiegelmers which may be used or generated according to the present invention directed against a target molecule, is based on a similar principle. The manufacture of spiegelmers is described in the international patent application WO 98/08856. Spiegelmers are L-nucleic acids, which means that they are composed of L-nucleotides rather than aptamers which are composed of D-nucleotides as aptamers are. Spiegelmers are characterized by the fact that they have a very high stability in biological system and, comparable to aptamers, specifically interact with the target molecule against which they are directed. In the purpose of generating spiegelmers, a heterogeneous population of D-nucleic acids is created and this population is contacted with the optical antipode of the target molecule, i.e. with the D-enantiomer of the naturally occurring L-enantiomer of the target molecule. Subsequently, those D-nucleic acids are separated which do not interact with the optical antipode of the target molecule. However, those D-nucleic acids interacting with the optical antipode of the target molecule are separated, optionally determined and/or sequenced and subsequently the corresponding L-nucleic acids are synthesized based on the nucleic acid sequence information obtained from the D-nucleic acids. These L-nucleic acids which are identical in terms of sequence with the aforementioned D-nucleic acids interacting with the optical antipode of the target molecule, will specifically interact with the naturally occurring target molecule rather than with the optical antipode thereof. Similar to the method for the generation of aptamers it is also possible to repeat the various steps several times and thus to enrich those nucleic acids specifically interacting with the optical antipode of the target molecule.

In a particular embodiment the cargo molecule is a short double-stranded oligodesoxynucleotide acting as a decoy molecule by specifically binding to transcription factors inside the cell. These decoy molecules are said to be taken up efficiently by cells without a need for specific carriers. It is expected that the efficiency and cytoplasmic delivery may be further enhanced by conjugation to a CPP according to the present invention In a particular embodiment the cargo molecule is an antibody.

The manufacture of an antibody is known to the one skilled in the art and, for example, described in Harlow, E., and Lane, D., "Antibodies: A Laboratory Manual," Cold Spring Harbor Laboratory, Cold Spring Harbor, N.Y., (1988). Preferably, monoclonal antibodies may be used in connection with the present invention which may be manufactured according to the protocol of Köhler and Milstein and further developments based thereon. Antibodies as used herein, include, but are not limited to, complete antibodies, antibody fragments or derivatives such as Fab fragments, Fc fragments and single-stranded antibodies, as long as they are suitable and capable of binding to protein kinase N beta. Apart from monoclonal antibodies also polyclonal antibodies may be used and/or generated. The generation of polyclonal antibodies is also known to the one skilled in the art and, for example, described in Harlow, E., and Lane, D., "Antibodies: A Laboratory Manual," Cold Spring Harbor Laboratory, Cold Spring Harbor, N.Y., (1988). Preferably, the antibodies used for therapeutical purposes are humanized or human antibodies as defined above.

The antibodies which may be used according to the present invention may have one or several markers or labels. Such markers or labels may be useful to detect the antibody either in its diagnostic application or its therapeutic application. Preferably the markers and labels are selected from the group comprising avidine, streptavidine, biotin, gold and fluorescein and used, e.g., in ELISA methods. These and further markers as well as methods are, e.g. described in Harlow, E., and Lane, D., "Antibodies: A Laboratory Manual," Cold Spring Harbor Laboratory, Cold Spring Harbor, N.Y. (1988).

It is also within the present invention that the label or marker exhibits an additional function apart from detection, such as interaction with other molecules. Such interaction may be, e.g., specific interaction with other compounds. These other compounds may either be those inherent to the system where the antibody is used such as the human or animal body or the sample which is analysed by using the respective antibody. Appropriate markers may, for example, be biotin or fluoresceine with the specific interaction partners thereof such as avidine and streptavidine and the like being present on the respective compound or structure to interact with the thus marked or labelled antibody.

In a particular embodiment the cargo molecule is a target specific binding peptide.

Such peptides may be generated by using methods according to the state of the art such as phage display. Basically, a library of peptide is generated, such as in form of phages, and this kind of libraries is contacted with the respective target molecule. Those peptides binding to the target molecule are subsequently removed, preferably as a complex with the target molecule, from the respective reaction. It is known to the one skilled in the art that the binding characteristics, at least to a certain extent, depend on the particularly realized experimental set-up such as the salt concentration and the like. After separating those peptides binding to the target molecule with a higher affinity or a bigger force, from the non-binding members of the library, and optionally also after removal of the target molecule from the complex of target molecule and peptide, the respective peptide(s) may subsequently be characterised. Prior to the characterisation optionally an amplification step is realized such as, e.g. by propagating the peptide coding phages. The characterisation preferably comprises the sequencing of the target binding peptides. Basically, the peptides are not limited in their lengths, however, preferably peptides having a lengths from about 8 to 20 amino acids are preferably obtained in the respective methods. The size of the libraries may be about $10^2$ to $10^{18}$, preferably $10^8$ to $10^{15}$ different peptides, however, is not limited thereto.

A particular form of target binding peptides are the so-called "anticalines" which are, among others, described in German patent application DE 197 42 706.

In a further aspect the invention is related to a nucleic acid coding for a peptide according to the present invention. Such nucleic acid can be easily derived by the ones skilled in the art based on the amino acid sequence of the peptide and the genetic code. It will be acknowledged that depending on the host organism the particular sequence can be adapted to the codon usage of the respective host organism. The nucleic acids sequence for the most preferred peptides according to the present invention can be taken from SEQ.ID.No. 26 and SEQ.ID.No. 27.

In a further aspect the invention is related to a nucleic acid coding for a peptide, whereby said peptide consists of a peptide according to the present invention and a further peptide or protein, and whereby said protein is generally referred to as fusion peptides/proteins. According to protocols known to those skilled in the art this nucleic acid may either serve the expression and purification of recombinant proteins, which as one part comprise the peptide(s) according to the present invention, or may be used in combination with suitable carriers in therapeutic strategies generally referred to as gene therapy. In a preferred embodiment the nucleic acid coding for the further peptide fused to the nucleic acid coding for the peptide according to the present invention, codes for a peptide serving as a peptide for vaccination. In another preferred embodiment the nucleic acid codes for a peptide, whereby the peptide preferably acts as a competitive inhibitor of molecular interactions inside the cell. In another preferred embodiment the nucleic acid codes for a peptide, whereby the peptide preferably acts as a substrate for an enzymatic reaction inside the cell. In another preferred embodiment the nucleic acid codes for the domain of a protein, whereby the domain preferably acts as a competitive inhibitor of molecular interactions inside the cell. In another preferred embodiment the nucleic acid codes for an enzyme, whereby the enzyme is preferably from the group of hydrolases.

In a still further aspect the invention is related to a fusion protein as defined herein and more particularly to a fusion protein encoded by a nucleic acid coding for a fusion protein in accordance with the present invention.

In a further aspect the present invention is related to a composition comprising either a complex according to the present invention, a composition comprising a peptide according to the present invention, a composition comprising a nucleic acid coding for a peptide according to the present invention, a composition comprising a peptide according to the present invention and a cargo molecule, a composition comprising a fusion protein according to the present invention, a composition comprising a nucleic acid coding for such fusion protein and a composition comprising human lactoferrin and a cargo molecule. It is within the skills of the one of the art that such compositions according to the present invention may comprise one or several of the peptides according to the present invention, one or several of the nucleic acids of the present invention, and/or one or several of the cargo molecules. In connection therewith it is preferred that the term "several" means several different species of the respective compounds or molecules. It will be well acknowledged by the ones skilled in the art that the composition typically comprises a multitude of the individual species of the peptide of the present invention, of the nucleic acid coding for such peptide and/or the of the cargo molecule. In connection therewith it is to be understood that any of the cargo molecules described herein can be used.

In a further aspect the present invention is related to the use of any of the compositions or constituents thereof described herein as transfection agent, as a medicament, as a diagnostic agent. In case the composition is used as a medicament or as a pharmaceutical composition, preferably the cargo molecule is a pharmaceutically active agent. Such pharmaceutically active agents may be a chemotherapeutic as for example daunorubicin or peptides interfering with molecular interactions inside the cell, or any of the molecules described herein as cargo molecules, whereby preferably said cargo molecules are pharmaceutically active or a pre-forms of such pharmaceutically active molecules. In case the composition is used as a diagnostic agent, preferably the cargo molecule is a diagnostic marker. Such diagnostic marker may be a fluorogenic substrate to detect the activity of a pathologically relevant protease, for example a caspase involved in the initiation and execution of apoptosis, inside the cell.

It is within the present invention that the peptides according to the present invention are preferably delivered to a specific type of cells or tissue or organ comprising such specific type of cells. In a preferred embodiment such specific delivery is mediated through a targeting moiety or targeting molecule which are, in their entirety, also referred to herein as the targeting entity.

In a more preferred embodiment, such targeting moiety is either part of the peptide according to the present invention or part of the cargo molecule. Alternatively or additionally, such targeting moiety is part of the complex or composition according to the present invention.

The targeting entity is preferably selected from the group comprising peptides, proteins, including antibodies, antibody fragments, single chain antibodies, aptamers, spiegelmers and ligands binding cell surface receptors. It will be acknowledged by the ones skilled in the art that in principle a partner moiety or molecule of any combination of interaction partners can be used which provides for a targeting, as a targeting entity. This includes the use of ligands to receptors which are expressed and more particularly overexpressed on a distinct cell type or ligands or molecules which are expressed and more particularly overexpressed on a distinct cell type. In the latter case a particularly prominent interaction partner thereof which acts as a targeting entity is selected from the group comprising antibodies, aptamers, spiegelmers, highly specific binding peptides, and anticalines. This kind of interaction partners and their specificity for a particular type of cell are known to the ones skilled in the art. Among others, the ErbB2 protein is specific for breast cancer cells. Accordingly, an antibody directed thereagainst is a suitable targeting entity.

In a preferred embodiment, the targeting moiety is included in or on the particles described herein which may be used as cargo molecules. Due to the size of such particles, the use of a more bulky targeting entity such as an antibody is preferable in connection with such embodiment.

In another preferred embodiment, the CPP, i.e. a peptide according to the present invention, is coupled to a moiety that intramolecularly masks the CPP and prevents the CPP from acting as a CPP. An enzymatically cleavable bond is incorporated between the CPP and the masking moiety. Such an intramolecular masking approach has been described for the targeting of a fluorophore conjugated to the CPP nonaarginine. The nonaarginine CPP was linked to a hexaglutamic acid stretch via a peptide linker corresponding to the cleavage site for matrix metalloproteinases 2 and 9. These proteases are secreted by tumor cells in high concentrations. Secretion of proteases selectively cleaves the CPP-mask construct in the vicinity of tumor cells, thereby enabling the efficient uptake of the CPP-cargo construct into the tumor cells. (T. Jiang et al., Proc. Natl. Acad. Sci, USA, 101, 17867-17872, 2004). Insofar, this embodiment represents an effective targeting or delivery means for tumor specific targeting and/or delivery.

Pharmaceutical compositions of the present invention may be manufactured by processes well known in the art; e.g., by means of conventional mixing, dissolving, granulating, dragee-making, levigating, emulsifying, encapsulating, entrapping or lyophilizing processes.

Pharmacological compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

Formulation that promote penetration of the epidermis are known in pharmacology, and can find use in the treatment of many skin conditions, such as, but not limited to, psoriasis and fungal infections. Formulations that promote penetration of the epidermis and underlying layers of skin are also known, and can be used to apply compositions of the present invention to, for example, underlying muscle or joints. In some preferred therapeutic embodiments, formulation comprising compositions of the present invention that deliver compounds for alleviation rheumatoid or osteo-arthritis can be administered by applying a cream, ointment or gel to the skin overlying the affected joint.

Oral and parenteral administration may be used where the peptide and/or complex is made stable enough to weather the harsh proteolytic environment of the gut. If so, the composition according to the present invention can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmacological preparations for oral use can made with the use of a solid excipient, optionally grinding the resulting mixture, and processing the mixture of granules, after adding suitable auxiliaries, if desired, to obtain tablets of dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragée cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solution, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may taken in the form of tablets or lozenges formulated in conventional manner. For the small peptides and complexes of the invention, this may prove useful.

For administration by inhalation, the composition according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The composition according to the present invention may be formulated for parenteral administration by injection, e.g., by bolus injection or continuous infusion. In this way it is also possible to target a particular organ, tissue, tumor site, site of inflammation, etc. Formulations for infection may be presented in unit dosage form, e.g., in ampoules or in multi-dose container, with an added preservative. The compositions may take such forms as suspensions, solutions or emulsions in oily or aqueous vehicles, and may contain formulatory agents such as suspending, stabilizing and/or dispersing agents.

Pharmaceutical compositions for parenteral administration include aqueous solutions of the compositions in water soluble form. Additionally, suspensions of the compositions may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compositions to allow for the preparation of highly concentrated solutions.

Alternatively, one or more components of the composition may be in powder form for constitution with a suitable vehicle, e.g., sterile pyrogen-fee water, before use.

The compositions may also be formulated in rectal compositions such as suppositories or retention enemas, e.g., containing conventional suppository bases such as cocoa butter or other glycerides.

In addition to the formulations described previously, the composition according to the present invention may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil), or as part of a solid or semi-solid implant that may or may not be auto-degrading in the body, or ion exchange resins, or one or more components of the composition can be formulated as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an amount effective to achieve its intended purpose. More specifically, a therapeutically effective amount means an amount of compound effective to prevent, alleviate or ameliorate symptoms of disease or prolong the survival of the subject being treated.

Determination of a therapeutically effective amount is within the capability of those skilled in the art, especially in light of the detailed disclosure provided herein.

For any compound used in the methods of the invention, the therapeutically effective amount or dose can be estimated initially from cell culture assays. For example, a dose can be formulated in animal models to achieve a circulating concentration range that includes the $IC_{50}$ as determined in cell culture (where inhibitor molecules are concerned). Such information can be used to more accurately determine useful doses in humans.

Toxicity and therapeutic efficacy of a composition of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage may vary within this range depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

The amount of composition administered will, of course, be dependent on the subject being treated, on the subject's weight, the severity of the affliction, the manner of administration and the judgment of the prescribing physician.

A pharmaceutical composition that comprises a peptide of a composition according to the present invention can be supplied such that the peptide and one or more of the cargo molecules are in the same container, either in solution, in suspension, or in powder form. The peptide according to the present invention can also be provided separately from one or more of the cargo molecules, and can be mixed with one or more of the cargo molecules prior to administration. Various packaging options are possible and known to the ones skilled in the art, depending, among others, on the route and mechanism of administration. For example, where the peptide according to the present is supplied separately from one or more of the cargo molecules, the compositions may, if desired, be presented in a pack having more than one chamber, and in which a barrier can be ruptured, ripped, or melted to provide mixing of the peptide according to the present invention with the cargo molecule. Alternatively, two separately provided elements can be mixed in a separate container, optionally with the addition to one or more other carriers, solutions, etc. One or more unit dosage forms containing the cargo molecule can be provided in a pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include any disease which may be treated or prevented or diagnosed using the compositions according to the present invention. In particular, the invention is ideally suited to gene therapy.

In a further aspect the present invention is related to a method for the treatment or prevention of a patient comprising the administration of a composition according to the present invention.

In a further aspect the present invention is related to a method for diagnosing a patient comprising the administration or use of a composition according to the present invention.

It is within the present invention that such nucleic acid coding for a peptide according to the present invention can be used as a vaccine or part of a vaccine. Preferably, the vaccine comprises a nucleic acid, more preferably an RNA, coding for an antigen which is suitable to elicit an immune response in a host organism, whereby the nucleic acid coding for a peptide according to the present invention and the nucleic acid coding for such antigen are administered to said host organism. Such administration may be done separately or in a combined manner. In a further embodiment, the respective nucleic acid may be contained or comprised in a vector, more preferably an expression vector which allows the expression of the nucleic acid(s) in said host organism. The further elements of such vector and in particular of such expression vector are known to the ones skilled in the art and comprise, among others one or several of the following elements: a promoter, an enhancer and a terminator. The antigen is preferably an antigen which is related to disease which is to be treated or prevented by the vaccine according to the present invention. In addition, the vaccine may also contain constituents exerting a so-called adjuvans effect and those acting as initiators of T helper cell responses.

In a still further embodiment, the present invention is related to a kit for transfection, for the treatment and/or prevention of a disease comprising a composition according to the present invention and, optionally one or several elements selected from the group comprising The present invention will now further be illustrated by reference to the following figures and examples from which further features, embodiments and advantages may be taken. In particular, FIG. 1 shows a diagram depicting the concentration dependant uptake of various CPPs labeled with carboxyfluorescein at their N-termini, expressed as extent of cell-associated fluorescence; hLF-peptide refers to a peptide consisting of amino acids 38 to 59 according to SEQ.ID.No. 1, bLF-peptide refers to a peptide consisting of amino acids 33 to 50 according to SEQ.ID.No. 2; cell associated fluorescence was determined by flow cytometry;

FIG. 2 shows a series of microphotographs obtained by confocal laser scanning microscopy indicating the concentration dependence of the intracellular distribution of the human lactoferrin-derived peptide and the bovine lactoferrin-derived peptide (see FIG. 1) at various concentrations;

FIG. 3A is a diagram showing the impact of various endocytosis inhibitors on the uptake of a fluorescein-labeled hLF-peptide (peptide sequence according to FIG. 1) with the fluorescein-hLF concentration being 5 µM (EIPA, 5-(N-Ethyl-N-isopropyl)amiloride; MβCD, Methyl-β-cyclodextrin; CPZ, Chlorpromazine); the uptake was determined by flow cytometry. Error bars represent the mean deviation of triplicates;

Figure 5:
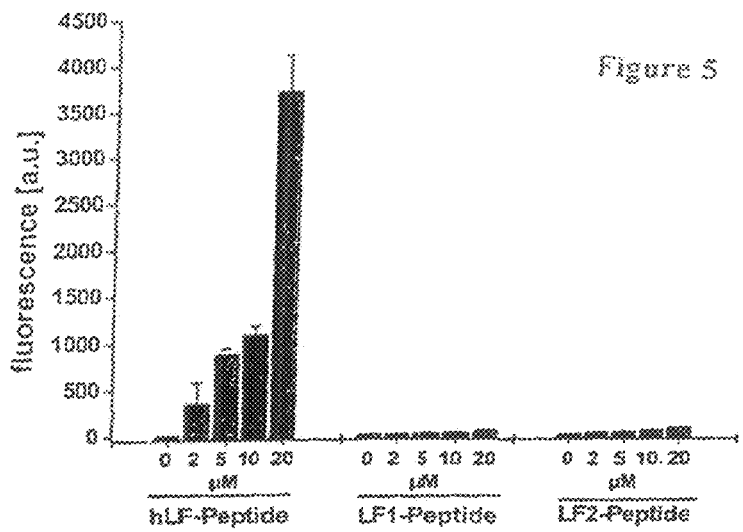
Figure 6:
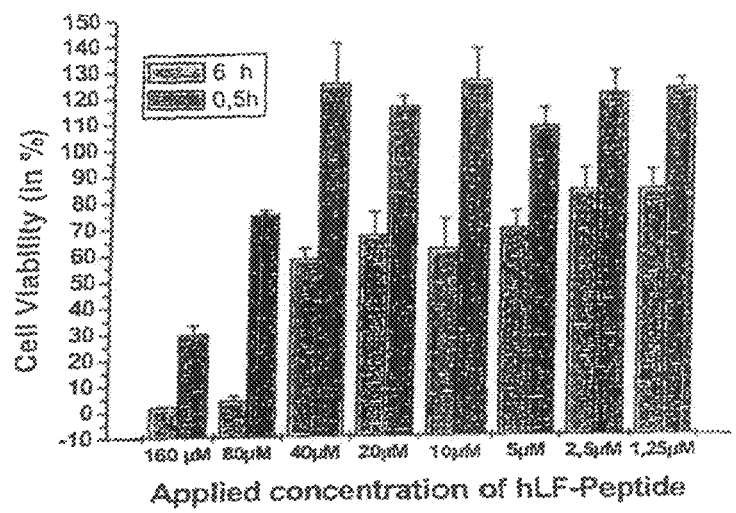

FIG. 5 is a diagram showing the extent of the uptake of the fluorescein-labeled hLF peptide corresponding to amino acids 38 to 59 according to SEQ.ID.No. 1 compared to truncated forms thereof illustrating the structure-activity relationship corresponding to amino acids 40 to 55 according to SEQ.ID.No. 1 (LF1-Peptide) and amino acids 40 to 50 according to SEQ.ID.No. 1 (LF2-Peptide); and FIG. 6 is a diagram depicting the cytotoxicity of the hLF peptide expressed as cell viability in percent at various concentrations of the fluorescein-labeled hLF peptide for HeLa cells incubated for different incubation times; for each pair of columns, the first column refers to cells incubated with peptide for 6 hours and the second column to cells incubated with peptide for 0.5 hours.

EXAMPLE 1

Experimental Procedures

Cells and Reagents.

The human cervical carcinoma cell line HeLa was obtained from the American Type Culture Collection (Manassas, Va.). HeLa cells were maintained in RPMI 1640 medium with stabilized glutamine and 2.0 g/L NaHCO$_3$ (PAN Biotech, Aidenbach, Germany) supplemented with 10% fetal calf serum (PAN Biotech). Chlorpromazine was from Calbiochem (Bad Soden, Germany), 5-(N-Ethyl-N-isopropyl) amiloride (EIPA), methyl-β-cyclodextrin (MβCD) and MTT [3-(4,5-dimethylthiazol-2-yl)-2,5-diphenyltetrazolium bromide] were obtained from Sigma (Deisenhofen, Germany).

Peptide Synthesis.

Peptides were purchased from EMC microcollections (Tübingen, Germany). The purity of all peptides was determined by analytical HPLC. The identity of the peptides was confirmed by MALDI-TOF mass spectrometry. Peptides with a purity of less than 85% were purified by preparative HPLC. Purity of all peptides used was >95% (214 nm HPLC). The peptides were N-terminally labelled with carboxyfluorescein as described (Fischer et al., Bioconjugate Chem. 14, 653-660, 2003).

Peptide Stock Solutions.

Peptides were dissolved in DMSO to concentrations of 10 mM. These stock solutions were further diluted in PBS or medium. Peptide concentrations of DMSO stock solutions were determined based on the absorption of carboxyfluorescein by UV/VIS-spectroscopy of a 1:100 dilution in 0.1 M Tris/HCl buffer (pH 8.8) with absorptions measured at 492 nm and assuming a molar extinction coefficient of carboxyfluorescein of 75,000 L/(mol·cm).

Flow Cytometry.

To determine the efficiency of peptide loading, HeLa cells were seeded at a density of 50,000 per well in 24-well plates (Sarstedt, Nümbrecht, Germany) in serum containing RPMI 1640. One day later, the cells were washed with medium and incubated in 300 μL RPMI 1640, containing peptides in the appropriate concentrations for 30 minutes. Each condition was tested in triplicate. After incubation, cells were washed with medium, detached by trypsinization for 5 minutes, suspended in ice-cold PBS containing 0.1% (w/v) BSA, and measured immediately by flow cytometry (BD FACS Calibur System, Becton Dickinson, Heidelberg, Germany). In each case, the fluorescence of 7,000 vital cells was acquired. Vital cells were gated based on sideward and forward scatter.

EXAMPLE 2

Uptake Efficiency of Peptides Derived from Human and Bovine Lactoferrin

The human and bovine lactoferrin-derived peptides were synthesized by solid-phase peptide synthesis. To detect uptake and the subcellular distribution in living cells, both peptides were labelled with carboxyfluorescein at the N-terminus. In order to determine whether the lactoferrin-derived peptides possessed activity as cell-penetrating peptides, the cell-associated fluorescence in HeLa cells incubated with bLF-Peptide or hLF-Peptide was determined by flow cytometry. Antp and the Tat-peptide were selected as well-established CPPs for comparison.

Figure 1:
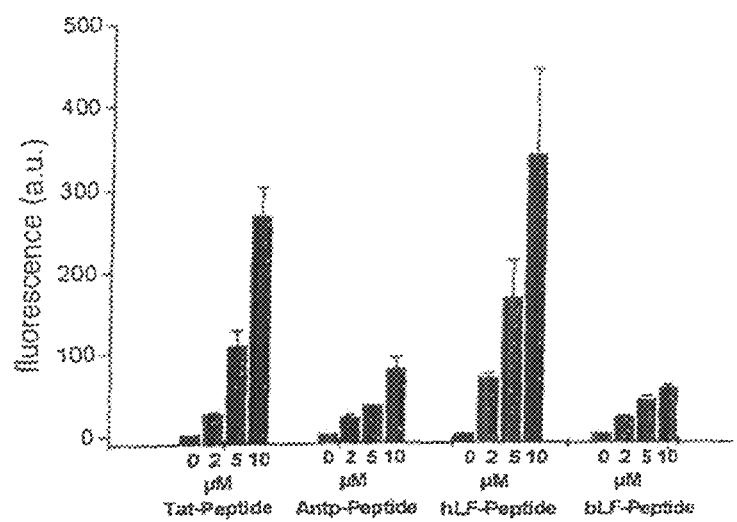
Figure 2:
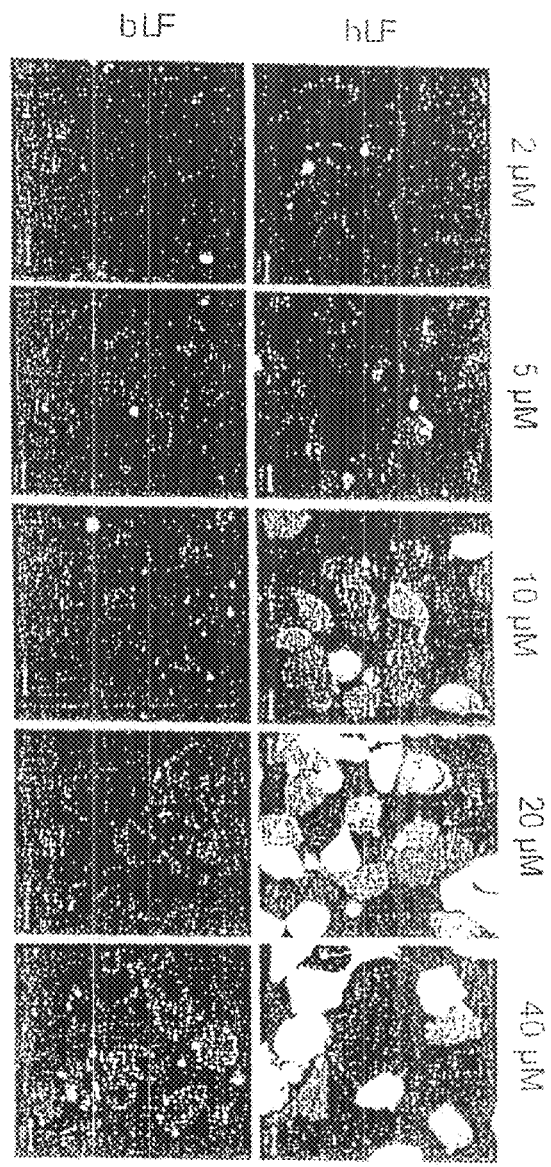
Figure 3:
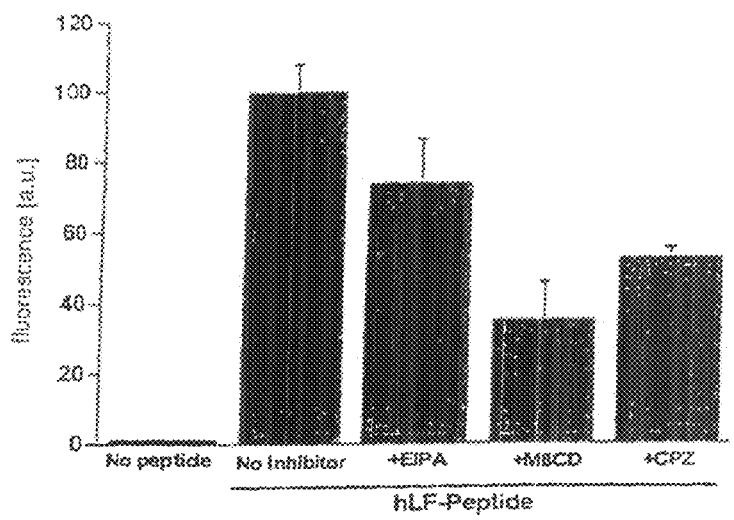
FIG. 3B is a diagram showing the impact of various endocytosis inhibitors on the uptake of a fluorescein-labeled hLF-peptide (peptide sequence according to FIG. 1) with the hLF concentration being 20 µM.
Figure 3:
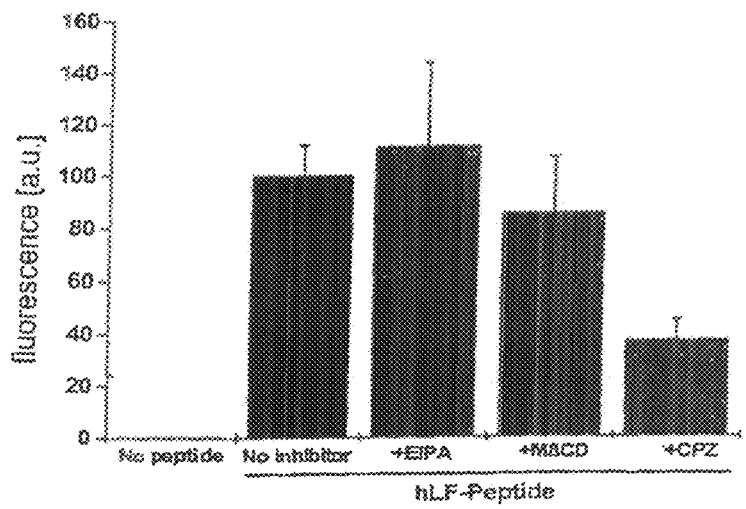
Figure 4:
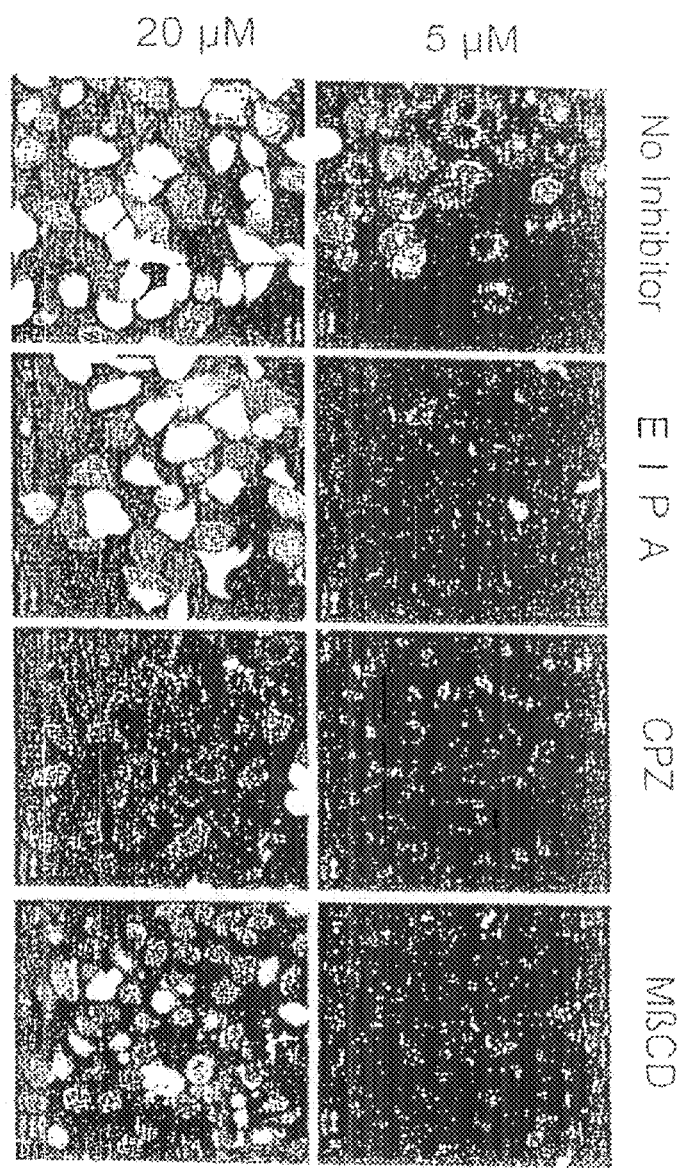
FIG. 4 shows pictures obtained by confocal laser scanning microscopy indicating the influences of endocytosis inhibitors on the uptake of fluorescein-labeled hLF-peptide at a peptide concentration of either 2 or 20 µM into HeLa cells.

For all four peptides, the cellular fluorescence, measured by flow cytometry, increased with peptide concentration as depicted in FIG. 1.

EXAMPLE 3

Structure-Activity Relationship

With 22 amino acids, the hLF-peptide is a CPP of intermediate length. Nonaarginine has only nine amino acids, the popular CPP transportan 27. Four of the seven cationic amino acids, and the aromatic amino acids are localized in the sequence nested within the cystein residues. In the full length protein, these cystein residue form a disulfide bridge that constrains the domain into a loop conformation. In addition, the cellular uptake of truncated peptides (LF1 and LF2, table 1) lacking the terminal cystein-residues was tested and compared to those containing the cystein residues.

TABLE 1

Primary structures of the peptides used in this study. All peptides were synthesized as peptide amides. Fluo represents 5(6)-carboxyfluorescein, CONH$_2$ the amidated C-terminus of the peptide.

| Entry | Peptide | Sequence |
|---|---|---|
| 1 | Tat-Peptide | Fluo-YGRKKRRQRRR-CONH$_2$ |
| 2 | Antp-Peptide | Fluo-RQIKIWFQNRRMKWKK-CONH$_2$ |
| 3 | hLF-Peptide | Fluo-KCFQWQRNMRKVRGPPVSCIKR-CONH$_2$ |
| 4 | bLF-Peptide | Fluo-PEWFKCRRWQWRMKKLGA-CONH$_2$ |
| 5 | LF1-Peptide | Fluo-FQWQRNMRKVRGPPVS-CONH$_2$ |
| 6 | LF2-Peptide | Fluo-FQWQRNMRKVR-CONH$_2$ |

The results are depicted in FIG. 5.

Uptake of both peptides lacking the cysteins was only about one tenth of the uptake of the hLF-peptide containing the two cysteine residues.

EXAMPLE 4

Cytoxicity of hLF-Peptide

In the experiments described above, using a concentration range of the hLF-peptide of up to 40 μM, no cytotoxic effects could be observed. However, for live cell microscopy of peptide uptake mostly rather short incubation times of less than one hour were employed. It was therefore also tested whether for longer incubation times and higher concentrations, the peptide affected cell viability. HeLa cells were incubated with the hLF-peptide at concentrations ranging from 1.25 μM to up to 160 μM for either 6 or 0.5 hours. Afterwards cell viability was determined using an MTT test. The result thereof are depicted in FIG. 6.

When cells were incubated with peptide for only 30 minutes, no cytotoxicity was observed for concentrations up to 40 μM. After 6 hours, the cell viability was slightly reduced for peptide concentrations higher than 5 μM. At concentrations higher than 40 μM all cells were killed.

The features of the present invention disclosed in the specification, the sequence listing, the claims and/or the drawings may both separately and in any combination thereof be material for realizing the invention in various forms thereof.

The invention claimed is:

1. A complex, comprising:
   (A) a peptide consisting of SEQ ID NO:3 and which is not-labeled with a radioactive label or a hapten; and
   (B) a cargo molecule non-covalently bound to the peptide, wherein the non-covalent bond is an ionic bond, a hydrogen bond, or a hydrophobic interaction.

2. The complex of claim 1, wherein the cargo molecule is at least one selected from the group consisting of a nucleic acid, an amino acid, a peptide, a protein, a carbohydrate, a lipid, and a small molecule.

3. The complex of claim 1, wherein the cargo molecule is present as or part of a structure,
   wherein the structure is selected from the group consisting of nanoparticles, microparticles, liposomes, and micelles.

4. The complex of claim 2, wherein the nucleic acid is a nucleic acid selected from the group consisting of DNA molecules, RNA molecules, PNA molecules, siRNA molecules, antisense molecules, ribozymes, aptamers, spiegelmers, and decoy molecules.

5. The complex of claim 2, wherein the cargo molecule is a peptide intended for use as a vaccine.

6. The complex of claim 2, wherein the nucleic acid is a nucleic acid-based vaccine.

7. The complex of claim 3, wherein the structure is at least one of the nanoparticles and the microparticles and the at least one of the nanoparticles and the microparticles comprise a pharmaceutically active compound.

8. The complex of claim 7, wherein at least one of the nanoparticles and the microparticles consist of a pharmaceutically active compound.

9. The complex of claim 1,
   wherein the cargo molecule is a small molecule having a molecular weight of 1000 D or less and is a drug or a drug candidate non-covalently bound to the peptide.

10. A complex, consisting of:
    (A) a peptide consisting of SEQ ID NO:3; and
    (B) a cargo molecule non-covalently bound to the peptide, wherein the non-covalent bond is an ionic bond, a hydrogen bond, or a hydrophobic interaction.

* * * * *